United States Patent [19]

Castellion et al.

[11] B 4,036,870

[45] July 19, 1977

[54] AMMOXIDATION OF ALKANES

[75] Inventors: George Augustus Castellion; William Frank Marzluff, both of Stamford, Conn.

[73] Assignee: American Cyanamid Company, Stamford, Conn.

[21] Appl. No.: 159,570

[22] Filed: July 2, 1971

[44] Published under the second Trial Voluntary Protest Program on March 23, 1976 as document No. B 159,570

[51] Int. Cl.$^2$ .................................................. C07C 120/14
[52] U.S. Cl. ........................... 260/465.3; 252/437; 252/454; 252/456; 252/458; 252/461; 252/467
[58] Field of Search ........................................ 260/465.3

[56] References Cited

U.S. PATENT DOCUMENTS

| | | | |
|---|---|---|---|
| 3,044,966 | 7/1962 | Callahan et al. | 260/465.3 UX |
| 3,118,928 | 1/1964 | Garrison, Jr. | 260/465.3 |
| 3,161,670 | 12/1964 | Adams et al. | 260/465.3 |
| 3,309,395 | 3/1967 | Nohe et al. | 260/465.3 |
| 3,365,482 | 1/1968 | Khoobiar | 260/465.3 |
| 3,433,823 | 3/1969 | McMahon | 260/465.3 |
| 3,518,295 | 6/1970 | Eden | 260/465.3 |
| 3,525,101 | 8/1970 | Young et al. | 260/465.3 |
| 3,532,734 | 10/1970 | Anderson et al. | 260/465.3 |
| 3,670,009 | 6/1972 | Taylor | 260/465.3 |

*Primary Examiner*—Joseph P. Brust
*Attorney, Agent, or Firm*—Gordon L. Hart

[57] ABSTRACT

In the catalytic reaction of saturated lower aliphatic hydrocarbons, e.g. propane, isobutane, with oxygen and ammonia in gas phase in contact with solid metal oxide catalysts, conversion of the hydrocarbon and selectivity of conversion to $\alpha,\beta$-unsaturated nitrile are improved by using a catalyst comprising a fluxing agent, e.g. phosphoric acid to maintain the catalytic metal oxide e.g. molybdenum oxide in a non-crystalline state.

6 Claims, No Drawings

AMMOXIDATION OF ALKANES

The invention relates to the preparation of α,β-unsaturated lower aliphatic nitriles by a process comprising catalytic ammoxidation of alkanes.

The invention is distinguishable from numerous processes for ammoxidation of olefins in which an unsaturated aliphatic hydrocarbon was converted to an unsaturated aliphatic nitrile. In the present invention the object is to convert alkanes, and particularly lower alkanes having 3 to about 9 carbon atoms, to corresponding α,β-unsaturated lower aliphatic nitriles. In preferred embodiments of the invention, propane is used as the starting hydrocarbon reactant for the production of acrylonitrile.

U.S. Pat. No. 3,365,482, patented Jan. 23, 1968 to S. Khoobiar, described a process for ammoxidation of alkanes to make α,β-unsaturated nitriles, using a catalyst consisting of molybdenum oxide or tungsten oxide supported on activated alumina. Catalysts reproduced according to descriptions in that patent are found by x-ray crystallography to have discernible definite crystalline structure in the catalyst phase, apart from the crystalline structure of the support. In catalysts of the present invention, if there is any crystalline structure in the solid catalyst phase, it is not discernible by x-ray crystallography. For this reason the solid catalysts of the invention are described as being non-crystalline solids. This same solid state is sometimes described as "amorphous" or "glassy" or "short range order only (SROO)". These non-crystalline catalysts produce substantially higher percentage conversion of alkane to α,β-unsaturated nitrile product, based on conversion of the hydrocarbon starting material, as compared with the crystalline metal oxide catalysts of the prior art.

According to the present invention, the catalyst for catalytic synthesis of α,β-unsaturated lower aliphatic nitriles by ammoxidation of alkanes comprises a non-crystalline solid phase comprising metal oxides selected from oxides of molybdenum, oxides of tungsten, oxides of niobium and oxides of tantalum, mixtures of those metal oxides and oxides of at least one of those metals mixed with oxides of chromium or vanadium, and further comprises a fluxing agent selected from phosphoric acid, boric acid, and antimony oxide present in amount sufficient to maintain the non-crystalline property of the solid catalyst. The most preferred catalysts are non-crystalline solids comprising oxides of molybdenum with phosphoric acid, the latter being present in amount sufficient to maintain the catalytic solids phase in the non-crystalline state. The catalyst may, in some of the preferred embodiments, further comprise a separate solid phase consisting essentially of a catalyst for ammoxidation of olefins, such as crystalline bismuth molybdate in definite crystalline form. In an even more preferred embodiment, bismuth oxide is present with the primary catalyst in the same short range order solid phase.

Some of the catalysts can be conveniently prepared by dissolving salts of the catalyst metals in aqueous or other liquid solution, then depositing the solution as a film or on a support and removing the solvent as by drying, then decomposing the deposited metal salts to produce the metal oxide catalyst. It is preferred that the fluxing agent be in an intimate mixture with the metal salts prior to calcining to produce the short range order solids as the finished catalyst. Without the fluxing agent the crystalline metal oxide solids would be produced, which, like the prior art catalysts would give inferior conversion and inferior selectivity of conversion to the unsaturated nitrile in the ammoxidation process.

The catalyst may be prepared and used without a support as by making the catalytic oxides in thin film and then breaking the solid film into particulate solid catalyst material, but the use of catalyst supports is preferred to improve the available surface area of catalyst per unit volume. Any of the conventional inert catalyst supports such as silica gel, various aluminas, kieselguhr, silica-alumina and the like will be suitable for the purpose. It is not necessary to select supports of unusually high surface area although such supports are quite suitable supports.

When the catalyst is prepared from metal salts which are deposited from aqueous solutions and then decomposed to the catalytic metal oxide, the decomposition may be accomplished by heating the deposited solid in an atmosphere containing oxygen at temperatures in the range from 400°C. to 600°C. Alternatively, when the catalyst is intended for use in the ammoxidation process, the process conditions for the ammoxidation reaction are also found suitable for the catalyst activation step, so the new catalyst can be conveniently finished by decomposition right in the same ammoxidation reactor where the catalyst is to be used, and this can be done even as the ammoxidation reaction is being carried out.

Molybdenum compounds and other primary catalyst metal compounds that can be used as precursors for the metal oxide catalysts include any compound that can be decomposed to the metal oxide by thermal decomposition. Preferred compounds for this use are water soluble compounds such as ammonium molybdate, ammonium paratungstate, ammonium phosphomolybdate, phosphotungstic acid, phosphomolybdic acid. In addition precipitation of metal oxides can be carried out from appropriate solutions of compounds such as $K_3NbO_4$, $K_3TaO_4$, $TaCl_5$, $NbCl_5$, $ZrO_2Cl_2$ etc. Mixtures of the aforementioned metal salt alone or with precipitated metal oxides can be used together to make catalysts of the mixed metal oxides. Salts of chromium or vanadium can be used in mixtures with one or several salts of the above-mentioned metal salts to make mixed metal oxide catalyst. Such mixed catalysts will have relatively lesser proportions of the chromium or vanadium oxide than of the other selected catalytic metals.

Phosphoric acid or another selected fluxing agent is intimately mixed with the metal salts and this can be done most conveniently by dissolving from about ½ mole to about 1 mole of the selected fluxing agent per gram atom of the catalytic metal in the aqueous solution. The solution is then used to impregnate a catalyst support, after which the solvent is removed as by drying, leaving a deposit of the salt and fluxing agent intimately mixed on the support surfaces. The salts and fluxing agent may be deposited separately from separate solutions and may be separately dried on the support, but a better catalyst is usually obtained by the single solution method. If the catalyst is to be calcined prior to use, it can be heated in an oven with a supply of air for a period of about 1 to about 10 hours at temperature in the range from about 400°C. to about 800°C.

The ammoxidation reaction for production of nitriles is carried out by contacting the reactants, as a gas phase comprising a mixture of the selected paraffin hydrocarbon of the class defined with ammonia and oxygen, with the solid phase catalyst at reaction temperature in the range from about 400°C. to about 600°C. The pressure at which the reaction is conducted is not critical and any convenient pressure may be used. We prefer to operate the reaction at about 1 atmosphere pressure and may operate with up to 3 or 4 atmospheres pressure in the reaction vessel with enough pressure drop through the vessel to drive the gases through the catalyst bed at the selected feed rate. The reaction temperature may be in the range from about 400°C. to about 550°C. and the optimum reaction temperature will usually be in the range from about 500°C. to 530°C.

The reaction is most conveniently carried out as a continuous process by passing the reactant gases through a bed of the catalyst which is in a suitable particulate form. Any of the various kinds of unit operations for gas-solids contacting may be used, such as fixed bed or fluidized bed catalytic reactors or the like. Contact time, defined as the volume of catalyst per volume of total reactants (at standard temperature and pressure) per second may be in the range from about 0.1 to about 10 seconds and the optimum contact time usually will be in the range from about 1 to about 6 seconds.

The molar feed ratio of the several reactants may have to be adjusted to obtain optimum yield of the $\alpha,\beta$-unsaturated nitrile product. Usually the optimum ratios will be about one mole of ammonia and about one mole of air (20% $O_2$) per mole of the selected alkane reactant. The ratios may be varied in the range from about 0.8 to about 3 moles ammonia and from about 1 to about 5 moles air per mole of the propane or other selected alkane reactant.

The catalytic process may produce a number of by-products such as carbon dioxide, olefins, saturated nitriles, miscellaneous hydrocarbons and the like. When propane is the selected reactant, for example, the $\alpha,\beta$-unsaturated nitrile product will be acrylonitrile; the by-products will include substantial yields of propylene and acetonitrile. An advantage of the present invention over prior art methods for ammoxidation of alkanes is the substantially increased conversion per pass of the alkane as well as the improved selectivity of conversion to the unsaturated nitrile product, both being factors of the substantially improved yield per pass based on the hydrocarbon feedstock. Furthermore, the ratio of saturated nitrile to unsaturated nitrile in the product stream is substantially decreased, indicating improved yield of the unsaturated nitrile based on the ammonia feedstock.

In one preferred embodiment of the invention the catalyst comprises molybdate of bismuth which alone is not an effective catalyst for conversion of alkanes to unsaturated nitriles but which is known to catalyze the conversion of olefins to unsaturated nitriles. Probably this secondary catalyst, viz. the bismuth molybdate functions in the reactor to convert the olefin that is produced as a by-product of the alkane ammoxidation to the unsaturated nitrile, thus increasing the ultimate yield of $\alpha,\beta$-unsaturated nitrile from the starting alkane feed reactant. This secondary catalyst may be present as a separate solid phase, even as a crystalline solid, but even better results are obtained when it is included in the same short range order solid phase that contains the primary catalyst for the alkane ammoxidation.

Following are examples illustrating the invention with detailed description of several most preferred embodiments and with description of certain processes that do not embody the invention but which are presented to point out certain advantages of the invention. Other processes not described in detail herein but nonetheless embodying the invention may be carried out according to the more general descriptions herein and within the broadest scope of the claims herein.

EXAMPLES OF CATALYST PREPARATION

EXAMPLE I

To 5.8 gm. bismuth nitrate dissolved in 50 ml. of 30% nitric acid is added 18 gm. 1/16 inch diameter dried alumina extrudates having surface area of 17 $m^2$/gm. selected for use as a support. After ten minutes the extrudates are removed from the solution and heated at 400°C. until brown fumes (nitrogen oxides) are no longer evolved. The product at this step is the support impregnated with oxide of bismuth, probably $Bi_2O_3$. In 65 ml. of deionized water are dissolved 34.6 gms. of $(NH_4)_6 Mo_7O_{24} \cdot 4H_2O$ and 10.3 grams of phosphoric acid and this solution is diluted to 100 ml. The bismuth impregnated extrudates are soaked in this solution for 10 minutes, the excess solution is decanted and the impregnated extrudates are again dried, this time at 120°C. for several hours. This gives a catalyst containing 9.3% Mo, 5.8% $PO_4$ and 2.4% Bi by weight. X-ray spectrometry reveals no discernible crystalline structure in the catalyst solids apart from the alumina support.

EXAMPLE II

Example I is repeated except that the bismuth impregnation step is omitted and the alumina support has surface area of 300 $M^2$/g.

EXAMPLE III

Example II is repeated except that the support is silica gel.

EXAMPLE IV

Example I is repeated except that the support is silica-alumina.

EXAMPLE V

In this example, catalysts according to the invention are prepared without using precursors for the oxides. A mixture of 15 gms. of $MoO_3$ and 4.9 gms. of $P_2O_5$ are heated in a furnace at 700°C. to 800°C. for one hour. The hot glass melt is poured into a cold carbon crucible and allowed to cool. The dark blue-black glass is ground to a powder. The ground powder is mixed with an equal weight of CABOSIL fine particulate silica for the catalyst support and the mixture is pressed into pellets. The pellets are then broken up and screened to make catalyst particles with particle sizes from 14–20 mesh.

EXAMPLE VI

Example V is repeated except that 3.01 gms. $Nb_2O_5$ are included with the $MoO_3$ and the mixture is heated to 910°C.

EXAMPLE VII

Extrudates made by the procedure in Example II are ground to powder and intimately mixed with an equal weight of powdered catalyst material consisting of bismuth molybdate on silica support. The mixture is pelleted and the pellets are broken up and screened to size.

AMMOXIDATION REACTIONS

A. Conversion of Propane

The reactions are carried out in small, quartz tubular reactors with fixed bed catalysts heated by wound resistance-wire electric furnaces. Catalyst samples are supported in the cylinder on small pieces of quartz wool. The reactions are carried out using 2 to 3 ml. of catalyst in fixed beds in 11 mm ID quartz tubes having a heated section about 20 cm. long. The upper part of the tube serves as the preheat zone. The furnaces are wound with resistance heating wires to provide a 12-13 cm. long uniform temperature zone in each furnace.

Ammonia, air and hydrocarbon are mixed in a manifold at room temperature in the selected proportions and metered from the manifold through the catalyst beds at predetermined feed rates. Reactor temperatures are monitored by thermocouples centrally located in the catalyst bed. Feed stock and product stream compositions are determined by gas liquid chromatography (GLC). Hydrocarbon conversion and product selectivity are calculated from the GLC measurements for each reaction.

The following terms are defined

Propane, ammonia and air are mixed in volume ratio of 1/1.5/7.2 and the mixture is fed through the reactor described above using the catalyst prepared in Example I. Pressure at the reactor outlet is one atmosphere. Residence time is 1.5 seconds. Reaction zone temperature is 529°C. Propane conversion is 44 percent with 54 percent selectivity of conversion to acrylonitrile, giving 23.7 percent yield of acrylonitrile, based on the hydrocarbon feed. Each of the catalysts prepared in Examples I–VII is used in the same manner for the same reaction except with some variations in residence time (RT) and reaction temperature as indicated in Table I. A control catalyst is also used in the same procedure for comparison to demonstrate the improvement of the present invention over the process using prior art catalysts. The control catalyst is crystalline oxide of molybdenum on alumina support, prepared by a procedure similar to Example II but without the use of phosphoric acid or other fluxing agent. This omission causes the catalytic oxide to be formed as a crystalline solid phase on the support.

B. Conversion of Isobutane

The procedure described above for the conversion of propane was followed except using isobutane instead of propane. Results obtained with isobutane using the catalyst prepared by Example II, are reported in Table II.

TABLE I

PROPANE

| Catalyst | Temperature °C. | RT Seconds | % Conversion Propane | % Selectivity Acrylonitrile | % Yield Acrylonitrile Per Pass |
|---|---|---|---|---|---|
| II | 550 | 3 | 35 | 26 | 9.2 |
| III | 550 | 2 | 29 | 24 | 7 |
| IV | 529 | 1.5 | 35 | 48 | 17 |
| V | 528 | 3 | 35 | 23 | 8.1 |
| VI | 532 | 2.2 | 33 | 24 | 7.9 |
| VII | 485 | 2 | 32 | 43 | 13.8 |
| I | 529 | 1.5 | 44 | 54 | 23.7 |
| $MoO_3/Al_2O_3$ | 550 | 1.5 | 29 | 4 | 1.5 |

TABLE II

ISOBUTANE

| Catalyst | Temperature °C. | RT Seconds | % Isobutane | % Selectivity Methacrylonitrile | % Yield Methacrylonitrile Per Pass |
|---|---|---|---|---|---|
| II | 508 | 3.5 | 40.4 | 58.4 | 23.6 |

The following terms are defined $$\text{Conversion, Percent} = \frac{\text{moles hydrocarbon reacted}}{\text{moles hydrocarbon fed}} \times 100$$

$$\text{Product Selectivity, Percent} = \frac{\text{moles product produced}}{\text{moles hydrocarbon reacted}} \times 100$$

$$\text{Yield, Percent} = \frac{\text{moles product produced}}{\text{moles hydrocarbon fed}} \times 100$$

$$\text{Space Velocity, hr}^{-1} = \frac{\text{volume of feed per hour at STP}}{\text{volume filled by catalyst in the reactor}}$$

Space velocities in the range from about 300 to about 1200 hr$^{-1}$ may be used.

$$\text{Residence Time (RT), Seconds} = \frac{17880 \times 60}{\text{reaction temp. °K}} \times \frac{1}{\text{Space Velocity}}$$

The several fold higher selectivity of conversion to acrylonitrile in reactions using the short range order catalysts as compared with the control catalyst demonstrates one advantage of the invention. The improved result obtained by the mixed bismuth, molybdenum oxide catalysts probably results in part from a secondary reaction in which bismuth catalyzes ammoxidation of propylene which is produced in the reactor as a by-product of the propane ammoxidation. Notice the higher yield with the Example I catalyst in which bismuth is included in the short range order phase as compared with that with the Example VII catalyst in which the bismuth is present as a separate crystalline solid phase. Without the presence of the primary catalyst which is molybdenum oxide in these examples, the bismuth oxide alone would not be significantly effective for converting propane to acrylonitrile.

Instead of the bismuth oxide component in the catalysts I and VII used for reactions outlined in Table I, one may substitute other catalysts that are useful for ammoxidation of propylene to acrylonitrile but those must be used in combination with the oxide of molybdenum or another selected metal oxide catalyst with phosphoric acid or other fluxing agent for the effective ammoxidation of propane according to the invention. Examples of such other secondary olefin ammoxidation catalysts which may be used in combination with the primary catalysts of this invention are those described in U.S. Pat. No. 3,365,482 and other patents referred to there, such as crystalline oxides of copper, tellurium, chromium, etc.

We claim:

1. A catalytic process for making $\alpha,\beta$-ethylenically-unsaturated lower aliphatic nitrile, said process comprising contacting a gas mixture comprising reactants ammonia, oxygen and lower alkane hydrocarbon having 3 to 4 carbon atoms, with a solid catalyst consisting essentially of mixed bismuth oxide and molybdenum oxide with at least said molybdenum oxide present entirely as a non-crystalline solid phase with phosphoric acid present as fluxing agent in said non-crystalline phase at reaction temperature in the range from about 400°C. to about 600°C. and residence time sufficient to effect the catalytic conversion of the lower alkane hydrocarbon to said nitrile.

2. A process defined by claim 1 wherein said bismuth oxide is a component of the same defined non-crystalline solid phase.

3. A catalytic process defined by claim 1 wherein the defined lower alkane hydrocarbon is propane and the defined nitrile product is acrylonitrile.

4. A catalytic process defined by claim 2 wherein the defined lower alkane hydrocarbon is propane and the defined nitrile product is acrylonitrile.

5. A catalytic process defined by claim 1 wherein the defined lower alkane hydrocarbon is isobutane and the defined nitrile product is methacrylonitrile.

6. A catalytic process defined by claim 2 wherein the defined lower alkane hydrocarbon is isobutane and the defined nitrile product is methacrylonitrile.

* * * * *